United States Patent
Srinivasan et al.

(10) Patent No.: US 12,227,506 B2
(45) Date of Patent: Feb. 18, 2025

(54) CRYSTALLINE POLYMORPHS OF 1-[(3R)-3-[4-AMINO-3-(4-PHENOXYPHENYL)-1H-PYRAZOLO[3,4-D]PYRIMIDIN-1-YL]-1-PIPERIDINYL]-2-PROPEN-1-ONE AND PROCESS FOR PREPARATION THEREOF

(71) Applicant: MSN LABORATORIES PRIVATE LIMITED, R&D CENTER, Telangana (IN)

(72) Inventors: Thirumalai Rajan Srinivasan, Hyderabad (IN); Eswaraiah Sajja, Hyderabad (IN); Vijayavitthal T Mathad, Hyderabad (IN); Rajeshwar Reddy Sagyam, Hyderabad (IN); Srinivasulu Rangineni, Hyderabad (IN); Venkata Narasayya Saladi, Hyderabad (IN)

(73) Assignee: MSN LABORATORIES PRIVATE LIMITED, R&D CENTER, Telangana (IN)

( * ) Notice: Subject to any disclaimer, the term of this patent is extended or adjusted under 35 U.S.C. 154(b) by 10 days.

(21) Appl. No.: 17/432,938

(22) PCT Filed: Feb. 19, 2020

(86) PCT No.: PCT/IN2020/050154
§ 371 (c)(1),
(2) Date: Aug. 23, 2021

(87) PCT Pub. No.: WO2020/170270
PCT Pub. Date: Aug. 27, 2020

(65) Prior Publication Data
US 2024/0199615 A1    Jun. 20, 2024

(51) Int. Cl.
C07D 487/04    (2006.01)
A61K 31/519    (2006.01)

(52) U.S. Cl.
CPC .......... *C07D 487/04* (2013.01); *A61K 31/519* (2013.01)

(58) Field of Classification Search
CPC ............................ A61K 31/519; C07D 487/04
See application file for complete search history.

(56) References Cited

FOREIGN PATENT DOCUMENTS

WO    WO-2016170545 A1 * 10/2016 ........... C07D 211/42
WO    WO-2016207172 A1 * 12/2016

* cited by examiner

*Primary Examiner* — Sarah Pihonak
(74) *Attorney, Agent, or Firm* — IP PUNDIT LLC

(57) ABSTRACT

The present invention relates to novel crystalline polymorphs of 1-[(3R)-3-[4-amino-3(4-phenoxy phenyl)-1H-pyrazolo[3,4-d]pyrimidin-1-yl]-1-piperidinyl]-2-propen-1-one represented by the following structural formula-1 and process for preparation thereof.

Formula-1

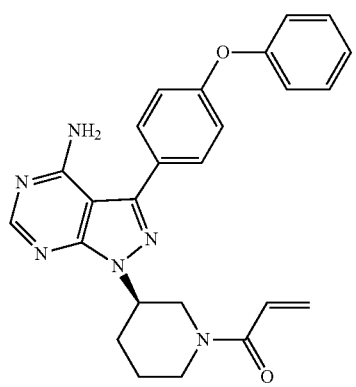

12 Claims, 4 Drawing Sheets

CRYSTALLINE POLYMORPHS OF 1-[(3R)-3-[4-AMINO-3-(4-PHENOXYPHENYL)-1H-PYRAZOLO[3,4-D]PYRIMIDIN-1-YL]-1-PIPERIDINYL]-2-PROPEN-1-ONE AND PROCESS FOR PREPARATION THEREOF

RELATED APPLICATIONS

This application claims the benefit of priority of our Indian patent applications 201941006555 filed on Feb. 19, 2019 and 201941039820 filed on Oct. 1, 2019 which are incorporated herein as reference.

FIELD OF THE INVENTION

The present invention provides novel crystalline polymorphs of 1-[(3R)-3-[4-amino-3-(4-phenoxyphenyl)-1H-pyrazolo[3,4-d]pyrimidin-1-yl]-1-piperidinyl]-2-propen-1-one compound of formula-1, which is represented by the following structural formula:

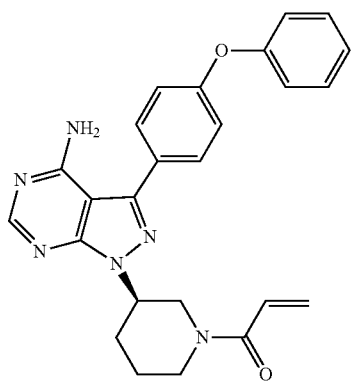

Formula-1

BACKGROUND OF THE INVENTION

1-[(3R)-3-[4-amino-3-(4-phenoxyphenyl)-1H-pyrazolo[3,4-d]pyrimidin-1-yl]-1-piperidinyl]-2-propen-1-one is commonly known as Ibrutinib. Ibrutinib is marketed under the brand name Imbruvica by Pharmacyclics Inc. It is approved in United States as Ibrutinib on Feb. 12, 2014. Ibrutinib is indicated for the treatment of patients with Mental cell lymphoma (MCL) who have received at least one prior therapy, Chronic lymphocytic leukemia (CLL) who have received at least one prior therapy.

U.S. Pat. No. 7,514,444 first discloses 1-[(3R)-3-[4-amino-3-(4-phenoxyphenyl)-1H-pyrazolo[3,4-d]pyrimidin-1-yl]-1-piperidinyl]-2-propen-1-one, its pharmaceutically acceptable salts and process for the preparation thereof.

PCT Publication No. WO 2013/184572 discloses various crystalline forms of compound of formula-1 designated as Form A, Form B, Form C, Form D, Form E, and Form F.

PCT Publication No. WO 2015/081180 discloses crystalline Form I of compound of formula-1.

CN103694241A discloses crystal form A of compound of formula-1.

CN103923084A discloses various crystalline forms of compound of formula-1 designated as Form II, Form III, Form IV, Form V, Form VI, Form VII and Form VIII.

WO 2015/145415A2 application discloses various solid forms of compound of formula-1 designated as Form III, Form IV, Form V, Form VI, Form VII, Form VIII and Form IX.

PCT Publication No. WO 2016/022942A1 discloses solid dispersions of compound of formula-1.

PCT Publication No. WO 2016/025720A1 discloses crystalline forms of compound of formula-1 designated as Form G, Form J and Form K.

US 20180051026 patent application discloses crystalline forms of compound of formula-1 designated as Form D1, Form D1a, Form D2, Form D2a, Form D3, Form D4, Form D5, Form D6, Form D7, Form D8, Form D9, Form D10, Form D11, Form D12 and Form D13

Polymorphism, the occurrence of different crystal forms, is a property of some molecules. When polymorphism occurs, the molecules arrange themselves in two or more different ways in the crystal, giving rise to differences in crystal structures and physical properties like melting point, thermal behaviors, X-ray powder diffraction (XRPD) pattern, infra-red absorption (IR) fingerprint, solid state nuclear magnetic resonance spectrum (NMR), and solubility and mechanical properties. Thus, the discovery of new polymorphic forms of a molecule is important in the development of pharmaceuticals, as they may provide materials having desirable processing properties, such as ease of handling, ease of processing, storage stability, ease of purification, improved dissolution profile, and/or improved shelf-life.

BRIEF DESCRIPTION OF THE INVENTION

The first aspect of the present invention is to provide novel crystalline polymorph of 1-[(3R)-3-[4-amino-3-(4-phenoxyphenyl)-1H-pyrazolo[3,4-d]pyrimidin-1-yl]-1-piperidinyl]-2-propen-1-one compound of formula-1, which is herein after designated as crystalline form-M1.

The second aspect of the present invention is to provide process for the preparation of crystalline form-M1 of 1-[(3R)-3-[4-amino-3-(4-phenoxyphenyl)-1H-pyrazolo[3,4-d]pyrimidin-1-yl]-1-piperidinyl]-2-propen-1-one compound of formula-1 The third aspect of the present invention is to provide novel crystalline polymorph of 1-[(3R)-3-[4-amino-3-(4-phenoxyphenyl)-1H-pyrazolo[3,4-d]pyrimidin-1-yl]-1-piperidinyl]-2-propen-1-one compound of formula-1, which is herein after designated as crystalline form-M2 and process for it's preparation.

The fourth aspect of the present invention is to provide novel crystalline polymorph of 1-[(3R)-3-[4-amino-3-(4-phenoxyphenyl)-1H-pyrazolo[3,4-d]pyrimidin-1-yl]-1-piperidinyl]-2-propen-1-one compound of formula-1, which is herein after designated as crystalline form-M3 and process for it's preparation.

The fifth aspect of the present invention is to provide crystalline polymorph of 1-[(3R)-3-[4-amino-3-(4-phenoxyphenyl)-1H-pyrazolo[3,4-d]pyrimidin-1-yl]-1-piperidinyl]-2-propen-1-one compound of formula-1, which is herein after designated as crystalline form-M4 and process for it's preparation.

The sixth aspect of the present invention is to provide novel crystalline polymorph of 1-[(3R)-3-[4-amino-3-(4-phenoxyphenyl)-1H-pyrazolo[3,4-d]pyrimidin-1-yl]-1-piperidinyl]-2-propen-1-one compound of formula-1, which is herein after designated as crystalline form-M5 and process for it's preparation.

The seventh aspect of the present invention is to provide novel crystalline polymorph of 1-[(3R)-3-[4-amino-3-(4-phenoxyphenyl)-1H-pyrazolo[3,4-d]pyrimidin-1-yl]-1-piperidinyl]-2-propen-1-one compound of formula-1, which is herein after designated as crystalline form-M6.

The eighth aspect of the present invention is to provide a process for the preparation of crystalline form-M5 of 1-[(3R)-3-[4-amino-3-(4-phenoxyphenyl)-1H-pyrazolo[3,4-d]pyrimidin-1-yl]-1-piperidinyl]-2-propen-1-one compound of formula-1.

DETAILED DESCRIPTION OF THE INVENTION

The term "suitable solvent" used in the present invention refers to "hydrocarbon solvents" such as n-pentane, n-hexane, n-heptane, cyclohexane, pet ether, benzene, toluene, xylene and the like; "ether solvents" such as dimethyl ether, diethyl ether, diisopropyl ether, methyl tert-butyl ether, 1,2-dimethoxyethane, tetrahydrofuran, 1,4-dioxane and the like; "ester solvents" such as methyl acetate, ethyl acetate, n-propyl acetate, isopropyl acetate, n-butyl acetate, isobutyl acetate, tert-butyl acetate and the like; "polar-aprotic solvents" such as dimethylacetamide, dimethylformamide, dimethylsulfoxide, N-methylpyrrolidone (NMP) and the like; "chloro solvents" such as dichloromethane, dichloroethane, chloroform, carbon tetrachloride and the like; "ketone solvents" such as acetone, methyl ethyl ketone, methyl isobutyl ketone and the like; "nitrile solvents" such as acetonitrile, propionitrile, isobutyronitrile and the like; "alcohol solvents" such as methanol, ethanol, n-propanol, iso-propanol, n-butanol, iso-butanol, t-butanol, ethane-1,2-diol, propane-1,2-diol and the like; "polar solvents" such as water; formic acid, acetic acid or mixture of any of the aforementioned solvents.

The first aspect of the present invention provides novel crystalline polymorph of 1-[(3R)-3-[4-amino-3-(4-phenoxyphenyl)-1H-pyrazolo[3,4-d]pyrimidin-1-yl]-1-piperidinyl]-2-propen-1-one compound of formula-1. The said novel crystalline polymorph is herein after designated as crystalline form-M1.

The crystalline form-M1 of compound of formula-1 of the present invention is characterized by its PXRD pattern having peaks at about 6.8 and 11.6±0.2° of 2θ.

The crystalline form-M1 of compound of formula-1 is further characterized by its PXRD pattern having peaks at about 17.6, 18.6, 20.5, 24.5 and 24.8±0.2° of 2θ.

In another embodiment, the crystalline form-M1 of compound of formula-1 is further characterized by its PXRD pattern having peaks at about 16.7, 22.6, 23.6 and 26.8±0.2° of 2θ.

Figure 1:
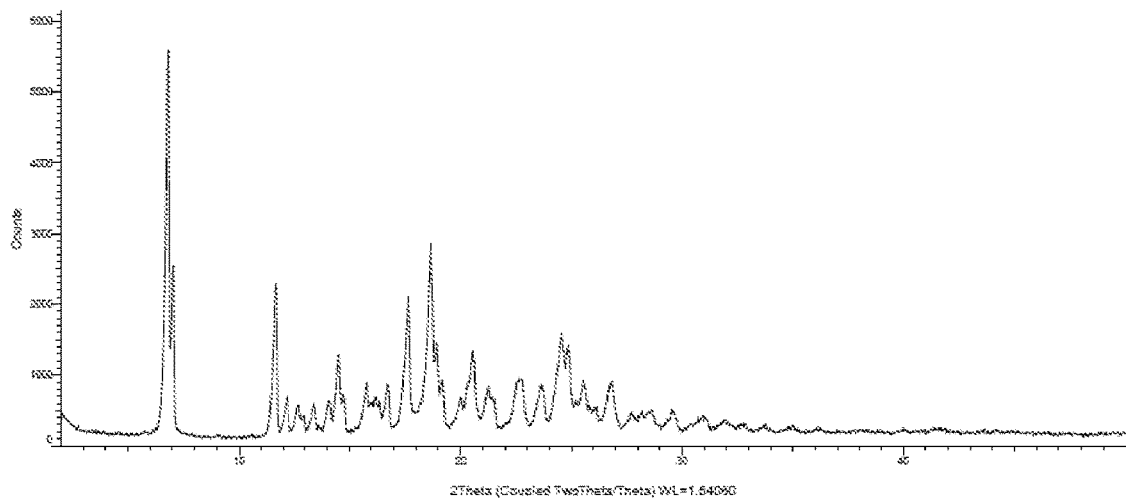
FIG. 1: Illustrates the PXRD pattern of crystalline form-M1 of compound of formula-1.

The crystalline form-M1 of compound of formula-1 of the present invention is further characterized by its PXRD pattern as illustrated in FIG. 1.

The second aspect of the present invention provides a process for the preparation of crystalline form-M1 of 1-[(3R)-3-[4-amino-3-(4-phenoxyphenyl)-1H-pyrazolo[3,4-d]pyrimidin-1-yl]-1-piperidinyl]-2-propen-1-one compound of formula-1, comprising:
a) providing a solution of compound of formula-1 in isopropanol optionally in mixture with a first solvent,
b) optionally filtering the obtained solution,
c) combining the solution with a second solvent at a suitable temperature to provide crystalline form-M1 of compound of formula-1.

In one embodiment of above step-a) providing a solution of compound of formula-1 can be done by combining compound of formula-1 with isopropanol optionally in mixture with a first solvent and optionally heating the reaction mixture to a suitable temperature ranging from about 25° C. to about 100° C.

The suitable first solvent can be selected from but not limited to polar solvents such as water, polar-aprotic solvents, alcohol solvents, ether solvents or mixtures thereof.

In step-c) the suitable second solvent can be selected from but not limited to ketone solvents, ester solvents, hydrocarbon solvents, chloro solvents, nitrile solvents or mixtures thereof, and the suitable temperature ranges from about −60° C. to about 100° C.

Preferred embodiment of the present invention provides a process for the preparation of crystalline form-M1 of compound of formula-1 comprising:
a) providing a solution of compound of formula-1 in a mixture of isopropanol and water
b) filtering the solution obtained in step-a),
c) combining the solution with n-heptane at about −50 to about −40° C. to provide crystalline form-M1 of compound of formula-1.

In step c) isolation of crystalline form-M1 can be carried out by removing the solvent by filtration at temperatures less than about 60° C., less than about 40° C., less than about 20° C. or less than about 0° C.

The third aspect of the present invention provides novel crystalline polymorph of 1-[(3R)-3-[4-amino-3-(4-phenoxyphenyl)-1H-pyrazolo[3,4-d]pyrimidin-1-yl]-1-piperidinyl]-2-propen-1-one compound of formula-1 & process for it's preparation. The said novel crystalline polymorph is herein after designated as crystalline form-M2.

Figure 2:
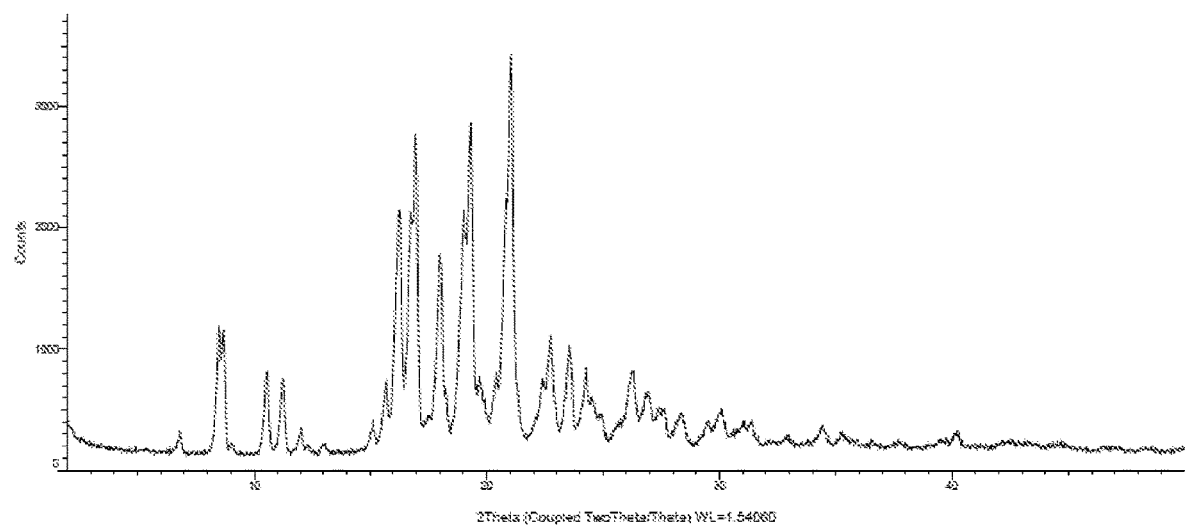
FIG. 2: Illustrates the PXRD pattern of crystalline form-M2 of compound of formula-1.

The said crystalline form-M2 of compound of formula-1 of the present invention is characterized by its PXRD pattern as illustrated in FIG. 2.

The third aspect of the present invention further provides a process for preparation of crystalline form-M2 of 1-[(3R)-3-[4-amino-3-(4-phenoxyphenyl)-1H-pyrazolo[3,4-d]pyrimidin-1-yl]-1-piperidinyl]-2-propen-1-one compound of formula-1, comprising:
a) providing a solution of compound of formula-1 in O-cresol,
b) optionally filtering the obtained solution,
c) combining the solution with a solvent at a suitable temperature to provide crystalline form-M2 of compound of formula-1.

In one embodiment of above step-a) providing a solution of compound of formula-1 can be done by combining compound of formula-1 with O-cresol and optionally heating the reaction mixture to a suitable temperature ranging from about 25° C. to about 100° C.

In step-c) a solvent can be selected from but not limited to ketone solvents, ester solvents, hydrocarbon solvents, chloro solvents, nitrile solvents, ether solvents or mixtures thereof, and the suitable temperature ranges from about −60° C. to about 100° C.

In step c) isolation of crystalline form-M2 can be carried out by removing the solvent by filtration at temperatures less than about 60° C., less than about 40° C., less than about 20° C. or less than about 0° C.

The fourth aspect of the present invention provides novel crystalline polymorph of 1-[(3R)-3-[4-amino-3-(4-phenoxyphenyl)-1H-pyrazolo[3,4-d]pyrimidin-1-yl]-1-piperidinyl]-2-propen-1-one compound of formula-1 & process for it's preparation. The said novel crystalline polymorph is herein after designated as crystalline form-M3.

Figure 3:
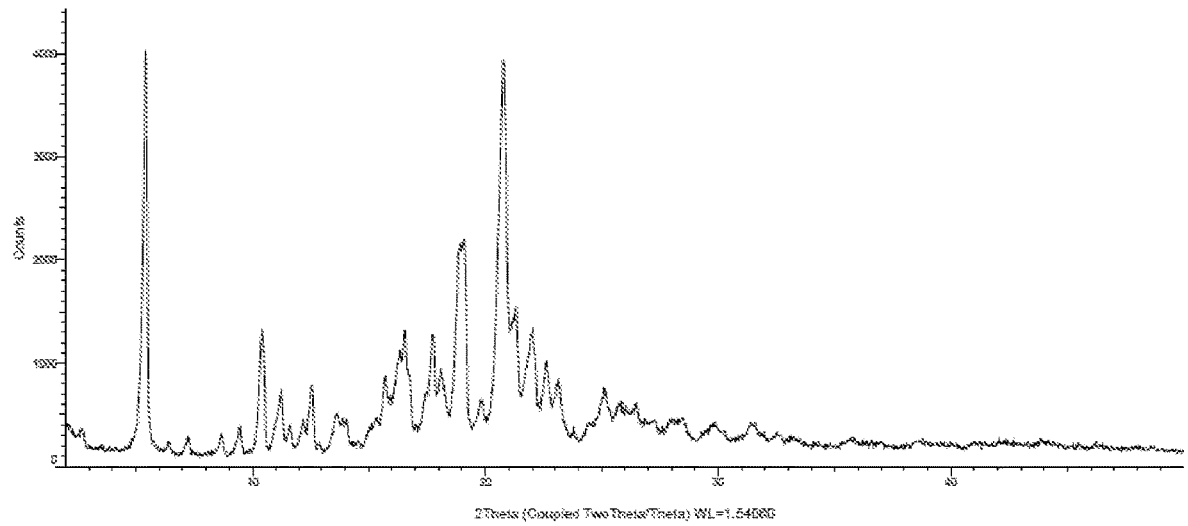
FIG. 3: Illustrates the PXRD pattern of crystalline form-M3 of compound of formula-1.

The said crystalline form-M3 of compound of formula-1 of the present invention is characterized by its PXRD pattern as illustrated in FIG. 3.

The fourth aspect of the present invention further provides a process for preparation of crystalline form-M3 of 1-[(3R)-3-[4-amino-3-(4-phenoxyphenyl)-1H-pyrazolo[3,4-d]pyrimidin-1-yl]-1-piperidinyl]-2-propen-1-one compound of formula-1, comprising:
a) providing a solution of compound of formula-1 in benzyl alcohol,
b) optionally filtering the obtained solution,
c) combining the solution with a solvent at a suitable temperature to provide crystalline form-M3 of compound of formula-1.

In one embodiment of above step-a) providing a solution of compound of formula-1 can be done by combining compound of formula-1 with benzyl alcohol and optionally heating the reaction mixture to a suitable temperature ranging from about 25° C. to about 100° C.

In step-c) a solvent can be selected from but not limited to ketone solvents, ester solvents, hydrocarbon solvents, chloro solvents, nitrile solvents, ether solvents or mixtures thereof, and the suitable temperature ranges from about −60° C. to about 100° C.

In step c) isolation of form-M3 can be carried out by removing the solvent by filtration at temperatures less than about 60° C., less than about 40° C., less than about 20° C. or less than about 0° C.

The fifth aspect of the present invention provides novel crystalline polymorph of 1-[(3R)-3-[4-amino-3-(4-phenoxyphenyl)-1H-pyrazolo[3,4-d]pyrimidin-1-yl]-1-piperidinyl]-2-propen-1-one compound of formula-1 & process for it's preparation.

The said novel crystalline polymorph is herein after designated as crystalline form-M4.

Figure 4:
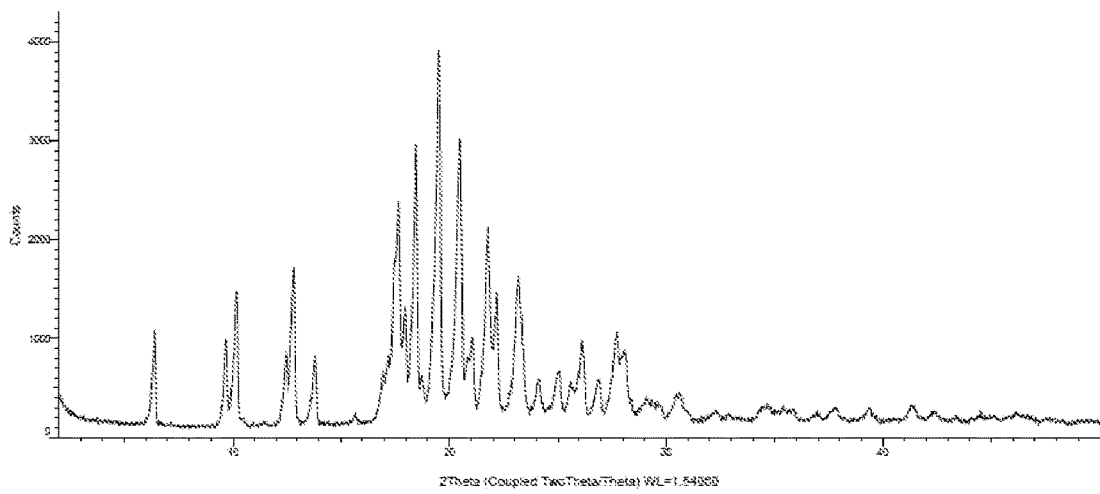
FIG. 4: Illustrates the PXRD pattern of crystalline form-M4 of compound of formula-1.

The said crystalline form-M4 of compound of formula-1 of the present invention is characterized by its PXRD pattern as illustrated in FIG. 4.

The fifth aspect of the present invention further provides a process for preparation of crystalline form-M4 of 1-[(3R)-3-[4-amino-3-(4-phenoxyphenyl)-1H-pyrazolo[3,4-d]pyrimidin-1-yl]-1-piperidinyl]-2-propen-1-one compound of formula-1, comprising:
a) providing a solution of compound of formula-1 in methyl benzoate,
b) optionally filtering the obtained solution,
c) optionally combining the solution with a solvent at a suitable temperature to provide crystalline form-M4 of compound of formula-1.

In one embodiment of above step-a) providing a solution of compound of formula-1 can be done by combining compound of formula-1 with methyl benzoate and optionally heating the reaction mixture to a suitable temperature ranging from about 25° C. to about 100° C.

In step-c) a solvent can be selected from but not limited to ketone solvents, ester solvents, hydrocarbon solvents, chloro solvents, nitrile solvents, ether solvents or mixtures thereof, and the suitable temperature ranges from about −60° C. to about 100° C.

Isolation of crystalline form-M4 can be carried out by removing the solvent by filtration at temperatures less than about 60° C., less than about 40° C., less than about 20° C. or less than about 0° C.

The sixth aspect of the present invention provides novel crystalline polymorph of 1-[(3R)-3-[4-amino-3-(4-phenoxyphenyl)-1H-pyrazolo[3,4-d]pyrimidin-1-yl]-1-piperidinyl]-2-propen-1-one compound of formula-1 & process for it's preparation.

The said novel crystalline polymorph is herein after designated as crystalline form-M5.

The crystalline form-M5 of compound of formula-1 of the present invention is characterized by its PXRD pattern having peaks at about 6.3, 10.0, 12.8, 13.7, 17.2, 18.1, 19.4, 20.2, 20.9, 21.6, 23.1, 23.7, 24.6, 26.2 and 27.7±0.2° of 2θ.

Figure 5:
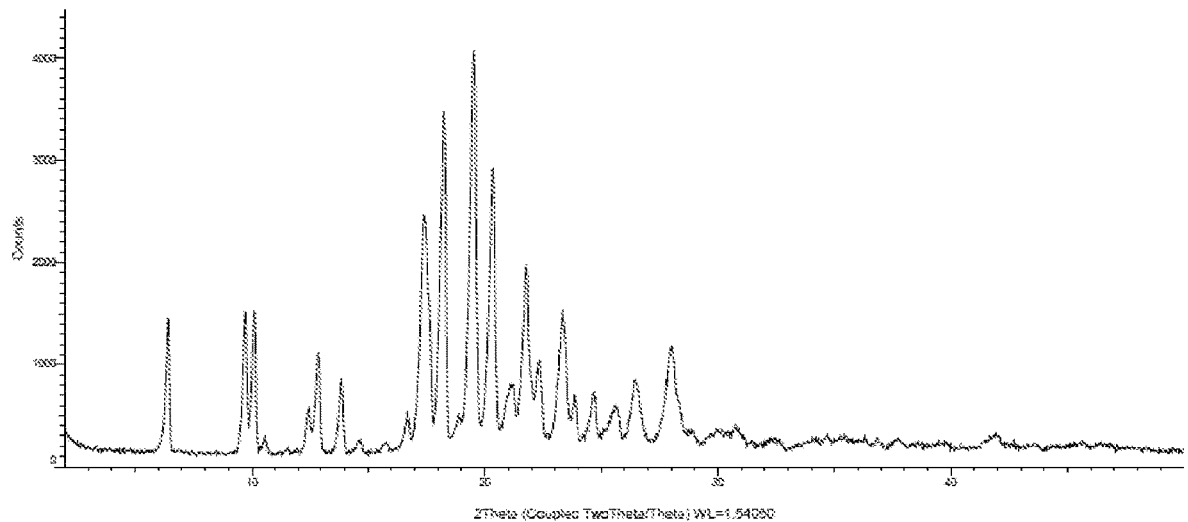
FIG. 5: Illustrates the PXRD pattern of crystalline form-M5 of compound of formula-1.

The said crystalline form-M5 of the present invention is characterized by its PXRD pattern as illustrated in FIG. 5.

The sixth aspect of the present invention further provides a process for preparation of crystalline form-M5 of 1-[(3R)-3-[4-amino-3-(4-phenoxyphenyl)-1H-pyrazolo[3,4-d]pyrimidin-1-yl]-1-piperidinyl]-2-propen-1-one compound of formula-1, comprising:
a) dissolving compound of formula-1 and methyl paraben in a solvent,
b) optionally filtering the obtained solution, and
c) isolating crystalline form-M5 of compound of formula-1.

In one embodiment of above step-a) dissolving the compound of formula-1 and methyl paraben can be done by combining compound of formula-1 and methyl paraben with a suitable solvent selected from alcohol solvents, ester solvents, nitrile solvents, ketone solvents, polar solvents, polar aprotic solvents, hydrocarbon solvents, ether solvents or mixture thereof, and optionally heating the reaction mixture to a suitable temperature ranging from about 25° C. to about 100° C.

In step-c) isolating the crystalline form-M5 can be done by cooling the reaction mixture to a suitable temperature ranges from about −60° C. to about 100° C. and filtering the precipitated solid.

In step c) isolation of crystalline form-M5 can be carried out by removing the solvent by filtration at temperatures less than about 60° C., less than about 40° C., less than about 20° C. or less than about 0° C.

The seventh aspect of the present invention provides novel crystalline polymorph of 1-[(3R)-3-[4-amino-3-(4-phenoxyphenyl)-1H-pyrazolo[3,4-d]pyrimidin-1-yl]-1-piperidinyl]-2-propen-1-one compound of formula-1 & process for it's preparation.

The said novel crystalline polymorph is herein after designated as crystalline form-M6.

The said crystalline form-M6 of the present invention is characterized by its PXRD pattern as illustrated in FIG. 1.

The seventh aspect of the present invention further provides a process for preparation of crystalline form-M6 of 1-[(3R)-3-[4-amino-3-(4-phenoxyphenyl)-1H-pyrazolo[3,4-d]pyrimidin-1-yl]-1-piperidinyl]-2-propen-1-one compound of formula-1, comprising:
a) suspending compound of formula-1 and methyl paraben in a solvent, and
b) isolating crystalline form-M6 of compound of formula-1.

In one embodiment of above step-a) suspending the compound of formula-1 and methyl paraben can be done by combining compound of formula-1 and methyl paraben with a suitable solvent selected from alcohol solvents, ester solvents, nitrile solvents, ketone solvents, polar solvents, polar aprotic solvents, hydrocarbon solvents, ether solvents or mixture thereof;

In step-b) isolating the crystalline form-M6 can be done by cooling the reaction mixture to a suitable temperature ranges from about −10° C. to about 25° C. and filtering the precipitated solid.

In step b) isolation of crystalline form-M6 can be carried out by removing the solvent by filtration at temperatures less than about 25° C., less than about 15° C., less than about 5° C. or less than about 0° C.

Preferred embodiment of the present invention provides a process for the preparation of crystalline form-M6 of compound of formula-1 comprising:
a) suspending compound of formula-1 and methyl paraben in a mixture of n-heptane and methyl tertiary butyl ether, and
b) isolating crystalline form-M6 of compound of formula-1.

In step b) isolation of crystalline form-M6 can be carried out by removing the solvent by filtration at temperatures less than about 25° C., less than about 15° C., less than about 5° C. or less than about 0° C.

Another preferred embodiment of the present invention provides a process for the preparation of crystalline form-M6 of compound of formula-1 comprising:
a) suspending compound of formula-1 and methyl paraben in a mixture of ethyl acetate and n-heptane, and
b) isolating crystalline form-M6 of compound of formula-1.

In step b) isolation of crystalline form-M6 can be carried out by removing the solvent by filtration at temperatures less than about 25° C., less than about 15° C., less than about 5° C. or less than about 0° C.

The eighth aspect of the present invention provides a process for the preparation of crystalline form-M5 of 1-[(3R)-3-[4-amino-3-(4-phenoxyphenyl)-1H-pyrazolo[3,4-d]pyrimidin-1-yl]-1-piperidinyl]-2-propen-1-one compound of formula-1, comprising:
a) suspending compound of formula-1 and methyl paraben in a solvent,
b) isolating crystalline form-M5 of compound of formula-1, and
c) optionally slurrying the material in water.

In one embodiment of above step-a) suspending the compound of formula-1 and methyl paraben can be done by combining compound of formula-1 and methyl paraben with a suitable solvent selected from alcohol solvents, ester solvents, nitrile solvents, ketone solvents, polar solvents, polar aprotic solvents, hydrocarbon solvents, ether solvents or mixture thereof;

In step-b) isolating the crystalline form-M5 can be done by cooling the reaction mixture to a suitable temperature ranges from about −10° C. to about 20° C. and filtering the precipitated solid.

In step b) isolation of crystalline form-M5 can be carried out by removing the solvent by filtration at temperatures less than about 60° C., less than about 40° C., less than about 20° C. or less than about 0° C.

Preferred embodiment of the present invention provides a process for the preparation of crystalline form-M5 of compound of formula-1 comprising:
a) suspending compound of formula-1 and methyl paraben in a mixture of ethyl acetate and n-heptane,
b) isolating crystalline form-M5 of compound of formula-1 from a reaction mixture at a suitable temperature, and
c) slurrying the material in water at a suitable temperature.

In step b) isolation of crystalline form-M5 can be carried out by removing the solvent by filtration at temperatures less than about 25° C., less than about 15° C., less than about 5° C. or less than about 0° C.

In step c) slurrying of compound is carried out at 25-30° C.

Another preferred embodiment of the present invention provides a process for the preparation of crystalline form-M5 of compound of formula-1 comprising:
a) suspending compound of formula-1 and methyl paraben in a mixture of n-heptane and methyl tertiary butyl ether, and
b) isolating crystalline form-M5 of compound of formula-1.

In step b) isolation of crystalline form-M5 can be carried out by removing the solvent by filtration at temperatures less than about 25° C., less than about 15° C., less than about 5° C. or less than about 0° C.

In the above processes, any polymorphic form of compound of formula-1 viz., crystalline form or amorphous form can be used as input for the preparation of crystalline form-M1, form-M2, form-M3, form-M4, form-M5 and form-M6 of compound of formula-1.

The crystalline forms of compound of formula-1 of the present invention are useful as input for preparation of other polymorphic forms of compound of formula-1 viz., crystalline polymorphs as well as amorphous form of compound of formula-1.

In one embodiment, the crystalline forms of the present invention may be present in the form of anhydrous, hydrates, solvates and/or co-crystals.

The crystalline form-M1, form-M2, form-M3, form-M4, form-M5 and form-M6 of compound of formula-1 of the present invention are useful for the preparation of various pharmaceutical compositions formulated in a manner suitable for the route of administration to be used where at least a portion of compound of formula-1 is present in the composition in particular any one of polymorphic form mentioned herein.

An embodiment of the present invention provides the use of crystalline form-M1, form-M2, form-M3, form-M4, form-M5 and form-M6 of compound of formula-1 of the present invention for the preparation of pharmaceutical formulations.

The other embodiment of the present invention provides pharmaceutical composition comprising one or more crystalline form-M1, form-M2, form-M3, form-M4, form-M5 and/or form-M6 of compound of formula-1 of the present invention and at least one pharmaceutically acceptable excipient, the said pharmaceutical composition is used for the treatment of patients with Mental cell lymphoma a (MCL) who have received at least one prior therapy, Chronic lymphocytic leukemia (CLL) who have received at least one prior therapy.

The 1-[(3R)-3-[4-amino-3-(4-phenoxyphenyl)-1H-pyrazolo[3,4-d]pyrimidin-1-yl]-1-piperidinyl]-2-propen-1-one compound of formula-1 which is used as starting material in the present invention can be prepared by any of the processes known in the art.

The crystalline form-M1, form-M2, form-M3, form-M4, form-M5 and form-M6 of compound of formula-1 obtained by the processes of the present invention can be further micronized or milled to achieve the desired particle size distribution in order to make suitable formulation. Techniques that may be used for particle size reduction includes but not limited to single or multi-stage micronization using cutting mills, pin/cage mills, hammer mills, jet mills, fluidized bed jet mills, ball mills and roller mills. Milling or micronization may be performed before drying or after drying of the product.

An embodiment of the present invention provides crystalline form-M1, form-M2, form-M3, form-M4, form-M5 and form-M6 of compound of formula-1 having particle size distribution of $D_{90}$ less than about 500 μm, preferably less than about 400 μm, more preferably less than about 300 μm, most preferably less than about 200 μm.

Another embodiment of the present invention provides crystalline form-M1, form-M2, form-M3, form-M4, form-M5 and form-M6 of compound of formula-1 having particle size distribution of $D_{90}$ less than about 100 μm, preferably less than about 50 μm, more preferably less than about 20 μm, most preferably less than about 10 μm.

The form-M1, form-M2, form-M3, form-M4, form-M5 and form-M6 of compound of formula-1 of the present invention are useful and suitable for the preparation of various pharmaceutical compositions formulated in a manner suitable for the route of administration to be used where at least a portion of compound of formula-1 is present in the composition in particular polymorphic form mentioned. Such pharmaceutical compositions may comprise compound of formula-1 present in the composition in a range of between 0.005% and 100% (wt/wt), with the balance of the pharmaceutical composition comprising additional substances such as excipients, diluents, lubricants, binders, wetting agents, disintegrating agents, glidants, sweetening agents, flavoring agents, emulsifying agents, solubilizing agents, pH buffering agents, perfuming agents, surface stabilizing agents, suspending agents and other conventional pharmaceutically inactive agents.

PXRD Method of Analysis:

The PXRD analysis of compounds of the present invention was carried out by using BRUKER/D8 ADVANCE X-Ray diffractometer using CuKα radiation of wavelength 1.5406A° and at a continuous scan speed of 0.03°/min.

The compound of formula-1 produced by the process of the present invention is having particle size distribution of $D_{90}$ less than 500 μm, preferably less than 250 μm, more preferably less than 100 μm.

An embodiment of the present invention provides compound of formula-1 with particle size distribution of $D_{90}$ less than 50 μm, preferably less than 20 μm, more preferably less than 15 μm.

The compound of formula-1 produced by the processes of the present invention can be further micronized or milled to get desired particle size to achieve desired solubility profile based on different forms of pharmaceutical composition requirements. Techniques that may be used for particle size reduction includes but not limited to single or multi-stage micronization using cutting mills, pin/cage mills, hammer mills, jet mills, fluidized bed jet mills, ball mills and roller mills. Milling or micronization may be performed before drying or after drying of the product.

The best mode of carrying out the present invention is illustrated by the below mentioned examples. These examples are provided as illustration only and hence should not be construed as limitation to the scope of the invention.

EXAMPLES

Example-1: Preparation of crystalline form-M1 of 1-[(3R)-3-[4-amino-3-(4-phenoxyphenyl)-1H-pyrazolo[3,4-d]pyrimidin-1-yl]-1-piperidinyl]-2-propen-1-one (Formula-1)

1.0 gm of 1-[(3R)-3-[4-amino-3-(4-phenoxyphenyl)-1H-pyrazolo[3,4-d]pyrimidin-1-yl]-1-piperidinyl]-2-propen-1-one was charged into the round bottom flask at 25-30° C. 30 ml of mixture of isopropyl alcohol and water was charged into the flask and the contents were heated to 50-60° C. The obtained solution was made particle free. In a separate flask, 60 ml of n-heptane was taken and cooled to −50° C. To this flask the above obtained 1-[(3R)-3-[4-amino-3-(4-phenoxyphenyl)-1H-pyrazolo[3,4-d]pyrimidin-1-yl]-1-piperidinyl]-2-propen-1-one solution was added and slowly raised the reaction mixture temperature to 0-5° C. Stirred the reaction mixture and filtered the precipitated solid. Dried the material to afford the title compound. Yield: 0.85 gm.

The PXRD pattern of the obtained compound is illustrated in FIG. 1.

Example-2: Preparation of crystalline form-M1 of 1-[(3R)-3-[4-amino-3-(4-phenoxyphenyl)-1H-pyrazolo[3,4-d]pyrimidin-1-yl]-1-piperidinyl]-2-propen-1-one (Formula-1)

50.0 gm of 1-[(3R)-3-[4-amino-3-(4-phenoxyphenyl)-1H-pyrazolo[3,4-d]pyrimidin-1-yl]-1-piperidinyl]-2-propen-1-one was charged into the round bottom flask at 25-30° C. 3000 ml of mixture of isopropyl alcohol and water was charged into the flask and the contents were heated to 50-60° C. The obtained solution was made particle free. In a separate flask, 2000 ml of n-heptane was taken and cooled to −60° C. To this flask the above obtained 1-[(3R)-3-[4-amino-3-(4-phenoxyphenyl)-1H-pyrazolo[3,4-d]pyrimidin-1-yl]-1-piperidinyl]-2-propen-1-one solution was added and slowly raised the reaction mixture temperature to 0-5° C. Stirred the reaction mixture and filtered the precipitated solid. Dried the material to afford the title compound. Yield: 42.0 gm.

The PXRD pattern of the obtained compound is illustrated in FIG. 1.

Example-3: Preparation of crystalline form-M2 of 1-[(3R)-3-[4-amino-3-(4-phenoxyphenyl)-1H-pyrazolo[3,4-d]pyrimidin-1-yl]-1-piperidinyl]-2-propen-1-one (Formula-1)

10.0 gm of 1-[(3R)-3-[4-amino-3-(4-phenoxyphenyl)-1H-pyrazolo[3,4-d]pyrimidin-1-yl]-1-piperidinyl]-2-propen-1-one was charged into the round bottom flask at 25-30° C. 80 ml of O-cresol was charged into the flask and the contents were stirred to get clear solution.

In a separate flask, 600 ml of mixture of n-heptane and methyl tertiary butyl ether was taken and cooled to −20° C. To this flask the above obtained 1-[(3R)-3-[4-amino-3-(4-phenoxyphenyl)-1H-pyrazolo[3,4-d]pyrimidin-1-yl]-1-piperidinyl]-2-propen-1-one solution was added and slowly raised the reaction mixture temperature to 20-25° C. Stirred the reaction mixture and filtered the precipitated solid. Dried the material to afford the title compound. Yield: 9.0 gm.

The PXRD pattern of the obtained compound is illustrated in FIG. 2.

Example-4: Preparation of crystalline form-M3 of 1-[(3R)-3-[4-amino-3-(4-phenoxyphenyl)-1H-pyrazolo[3,4-d]pyrimidin-1-yl]-1-piperidinyl]-2-propen-1-one (Formula-1)

5.0 gm of 1-[(3R)-3-[4-amino-3-(4-phenoxyphenyl)-1H-pyrazolo[3,4-d]pyrimidin-1-yl]-1-piperidinyl]-2-propen-1-one was charged into the round bottom flask at 25-30° C. 20 ml of benzyl alcohol was charged into the flask and the contents were stirred to get clear solution. A mixture of n-heptane and methyl tertiary butyl ether was added to the above solution and stirred the reaction mixture at 25-30° C. Filtered the precipitated solid and dried the material to afford the title compound. Yield: 4.5 gm.

The PXRD pattern of the obtained compound is illustrated in FIG. 3.

Example-5: Preparation of crystalline form-M4 of 1-[(3R)-3-[4-amino-3-(4-phenoxyphenyl)-1H-pyrazolo[3,4-d]pyrimidin-1-yl]-1-piperidinyl]-2-propen-1-one (Formula-1)

Procedure-1: 500 mg of 1-[(3R)-3-[4-amino-3-(4-phenoxyphenyl)-1H-pyrazolo[3,4-d]pyrimidin-1-yl]-1-piperidinyl]-2-propen-1-one was charged into the round bottom flask at 25-30° C. 2.5 ml of methyl benzoate was charged into the flask and the contents were stirred to get clear solution. 10 ml of n-heptane was added and stirred the reaction mixture. Filtered the precipitated solid and dried to afford the title compound. Yield: 450 mg.

The PXRD pattern of the obtained compound is illustrated in FIG. 4.

Procedure-2: 250 mg of 1-[(3R)-3-[4-amino-3-(4-phenoxyphenyl)-1H-pyrazolo[3,4-d]pyrimidin-1-yl]-1-piperidinyl]-2-propen-1-one was charged into the round bottom flask at 25-30° C. 0.7 ml of methyl benzoate was charged into the flask and the contents were stirred to get clear solution. Further stirred the reaction mixture until solid precipitated. Filtered the precipitated solid and dried to afford the title compound. Yield: 200 mg.

The PXRD pattern of the obtained compound is illustrated in FIG. 4.

Example-6: Preparation of crystalline form-M5 of 1-[(3R)-3-[4-amino-3-(4-phenoxyphenyl)-1H-pyrazolo[3,4-d]pyrimidin-1-yl]-1-piperidinyl]-2-propen-1-one (Formula-1)

Procedure-1: 20 gm of 1-[(3R)-3-[4-amino-3-(4-phenoxyphenyl)-1H-pyrazolo[3,4-d]pyrimidin-1-yl]-1-piperidinyl]-2-propen-1-one was charged into the round bottom flask at 25-30° C. 8.1 gm of methyl paraben and 200 ml of ethyl acetate were charged into the flask and the contents were heated to 55-65° C. The obtained solution was made particle free. Cooled the solution to 25-30° C. and stirred for 2 hours at same temperature. Filtered the precipitated solid and dried the material to afford the title compound. Yield: 13.0 gms.

The PXRD pattern of the obtained compound is illustrated in FIG. 5.

Procedure-2: 1 gm of 1-[(3R)-3-[4-amino-3-(4-phenoxyphenyl)-1H-pyrazolo[3,4-d]pyrimidin-1-yl]-1-piperidinyl]-2-propen-1-one was charged into the round bottom flask at 25-30° C. 410 mg of methyl paraben and 10 ml of ethyl acetate were charged into the flask and the contents were heated to 65-70° C. The obtained solution was made particle free. Cooled the solution to 25-30° C. and stirred for 1 hour at same temperature. Filtered the precipitated solid and dried the material to afford the title compound. Yield: 540 mg.

The PXRD pattern of the obtained compound is illustrated in FIG. 5.

Procedure-3: 500 mg of 1-[(3R)-3-[4-amino-3-(4-phenoxyphenyl)-1H-pyrazolo[3,4-d]pyrimidin-1-yl]-1-piperidinyl]-2-propen-1-one was charged into the round bottom flask at 25-30° C. 153 mg of methyl paraben and 10 ml of acetonitrile were charged into the flask and the contents were heated to 55-65° C. The obtained solution was made particle free. Cooled the solution to 25-30° C. and stirred for 1 hour at same temperature. Filtered the precipitated solid and dried the material to afford the title compound. Yield: 450 mg.

The PXRD pattern of the obtained compound is illustrated in FIG. 5.

Procedure-4: 20 gm of 1-[(3R)-3-[4-amino-3-(4-phenoxyphenyl)-1H-pyrazolo[3,4-d]pyrimidin-1-yl]-1-piperidinyl]-2-propen-1-one was charged into the round bottom flask at 25-30° C. 8.1 gm of methyl paraben and 200 ml of acetonitrile were charged into the flask and the contents were heated to 55-65° C. The obtained solution was made particle free. Cooled the solution to 25-30° C. and stirred for 2 hours at same temperature. Filtered the precipitated solid and dried the material to afford the title compound. Yield: 19.0 gms.

The PXRD pattern of the obtained compound is illustrated in FIG. 5.

Example-7: Preparation of crystalline form-M6 of 1-[(3R)-3-[4-amino-3-(4-phenoxyphenyl)-1H-pyrazolo[3,4-d]pyrimidin-1-yl]-1-piperidinyl]-2-propen-1-one (Formula-1)

Procedure-1: 5 gm of 1-[(3R)-3-[4-amino-3-(4-phenoxyphenyl)-1H-pyrazolo[3,4-d]pyrimidin-1-yl]-1-piperidinyl]-2-propen-1-one was charged into the round bottom flask at 25-30° C. 3.45 gm of methyl paraben and 150 ml of mixture of n-heptane and methyl tertiary butyl ether (1:1) were charged into the flask and the contents were cooled to 0-5° C. Stirred the reaction mixture for 8 to 10 hours. Filtered the precipitated solid and dried the material to afford the title compound. Yield: 4.0 gms.

Figure 6:
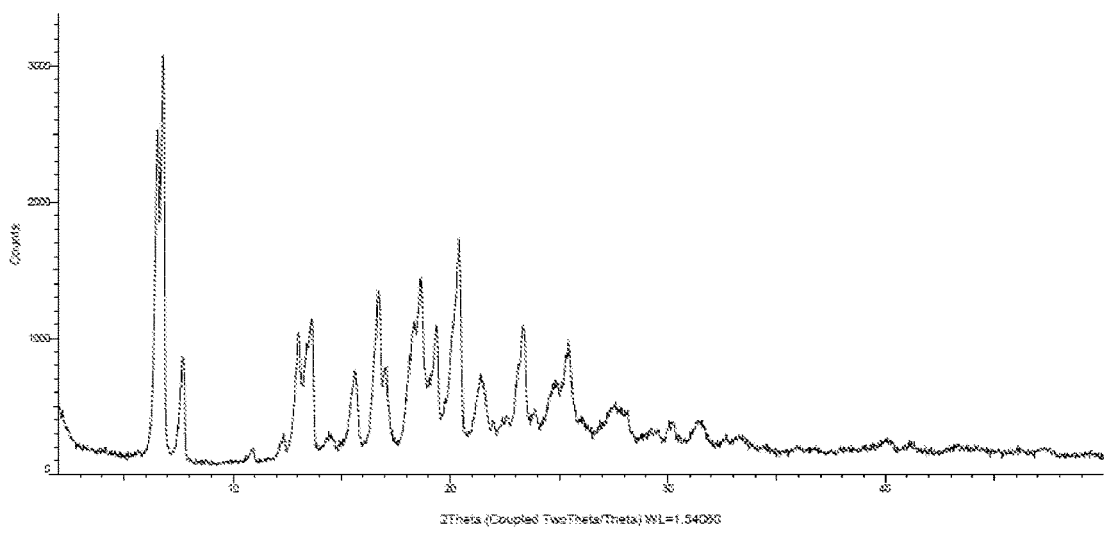
FIG. 6: Illustrates the PXRD pattern of crystalline form-M6 of compound of formula-1.

The PXRD pattern of the obtained compound is illustrated in FIG. 6.

Procedure-2: 0.5 gm of 1-[(3R)-3-[4-amino-3-(4-phenoxyphenyl)-1H-pyrazolo[3,4-d]pyrimidin-1-yl]-1-piperidinyl]-2-propen-1-one was charged into the round bottom flask at 25-30° C. 0.1725 gm of methyl paraben and 10 ml of mixture of n-heptane and ethyl acetate (8:2) were charged into the flask and the contents were cooled to 0-5° C. Stirred the reaction mixture for 2 to 3 hours at same temperature. Filtered the precipitated solid and dried the material to afford the title compound. Yield: 400 mg.

The PXRD pattern of the obtained compound is illustrated in FIG. 6.

Example-8: Preparation of crystalline form-M5 of 1-[(3R)-3-[4-amino-3-(4-phenoxyphenyl)-1H-pyrazolo[3,4-d]pyrimidin-1-yl]-1-piperidinyl]-2-propen-1-one (Formula-1)

Procedure-1: 5 gm of 1-[(3R)-3-[4-amino-3-(4-phenoxyphenyl)-1H-pyrazolo[3,4-d]pyrimidin-1-yl]-1-piperidinyl]-2-propen-1-one was charged into the round bottom flask at 25-30° C. 1.7 gm of methyl paraben and 100 ml of mixture of ethyl acetate and n-heptane (1:1) were charged into the flask and the contents were cooled to 0-5° C. Stirred the reaction mixture for 2 to 3 hours at 0-5° C. Filtered the precipitated solid. 80 ml of water was charged to the obtained solid and stirred for 2 hours at 25-30° C. Filtered the solid and dried the material to afford the title compound. Yield: 3.7 gms.

Figure 7:
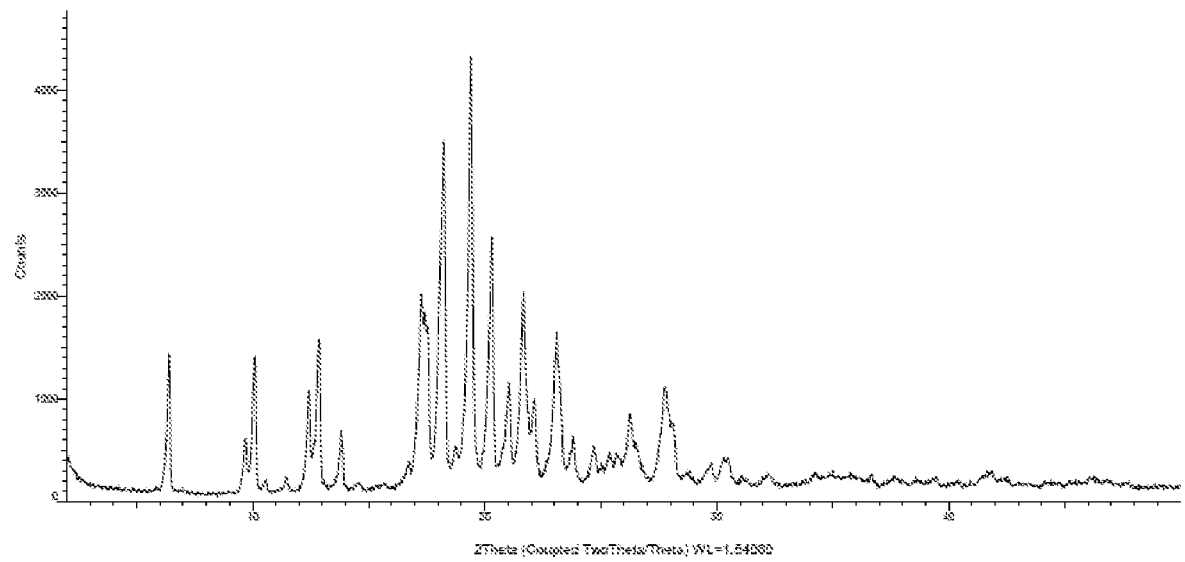
FIG. 7: Illustrates the PXRD pattern of crystalline form-M5 of compound of formula-1.

The PXRD pattern of the obtained compound is illustrated in FIG. 7.

Procedure-2: 5 gm of 1-[(3R)-3-[4-amino-3-(4-phenoxyphenyl)-1H-pyrazolo[3,4-d]pyrimidin-1-yl]-1-piperidinyl]-2-propen-1-one was charged into the round bottom flask at 25-30° C. 1.7 gm of methyl paraben and 100 ml of mixture of n-heptane and methyl tertiary butyl ether (MTBE) (1:1) were charged into the flask and the contents were cooled to 0-5° C. Stirred the reaction mixture for 5 to 8 hours. Filtered the precipitated solid and dried the material to afford the title compound. Yield: 3.6 gms.

The PXRD pattern of the obtained compound is illustrated in FIG. 7.

Example-9: Preparation of crystalline form-M5 of 1-[(3R)-3-[4-amino-3-(4-phenoxyphenyl)-1H-pyrazolo[3,4-d]pyrimidin-1-yl]-1-piperidinyl]-2-propen-1-one (Formula-1)

34.5 gms of methylparaben and 400 ml of methyl tertiary butyl ether (MTBE) were charged into the round bottom flask at 25-30° C. Heated the reaction mixture to 40-45° C. and stirred for 15 minutes. Filtered the reaction mixture and 1000 ml of n-heptane was added to the filtrate. Cooled the reaction mixture to 0-5° C. and stirred for 30 minutes. 100 gms of 1-[(3R)-3-[4-amino-3-(4-phenoxyphenyl)-1H-pyrazolo[3,4-d]pyrimidin-1-yl]-1-piperidinyl]-2-propen-1-one was charged into the above reaction mixture at 0-5° C. and stirred for 30 minutes. 600 ml of methyl tertiary butyl ether (MTBE) was charged into the above reaction mixture and the contents were stirred for 45 minutes at 0-5° C. Raised the temperature of the reaction mixture to 25-30° C. and stirred the reaction mixture for 5 to 6 hours. Filtered the precipitated solid, washed with mixture of n-heptane and methyl tertiary butyl ether (1:1) and dried the material to afford the title compound. Yield: 107 gms.

The PXRD pattern of the obtained compound is illustrated in FIG. 7.

We claim:

1. A crystalline form-M5 of 1-[(3R)-3-[4-amino-3-(4-phenoxyphenyl)-1H-pyrazolo[3,4-d]pyrimidin-1-yl]-1-piperidinyl]-2-propen-1-one compound of formula-1

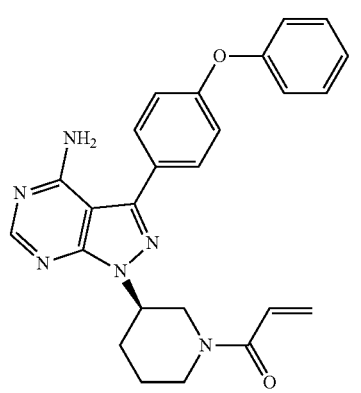

Formula-1 characterized by its PXRD pattern peaks at about 6.3, 10.0, 12.8, 13.7, 17.2, 18.1, 19.4, 20.2, 20.9, 21.6, 23.1, 23.7, 24.6, 26.2 and 27.7±0.2° of 2θ.

2. A process for the preparation of crystalline form-M5 according to claim 1, comprising:
   a) suspending compound of formula-1 and methyl paraben in a solvent,
   b) isolating crystalline form-M5 of compound of formula-1, and
   c) optionally slurrying the material in water.

3. The process for preparation according to claim 2, wherein the solvent is selected from alcohol solvents, ester solvents, nitrile solvents, ketone solvents, polar solvents, polar aprotic solvents, hydrocarbon solvents, ether solvents or mixture thereof; and optionally heating the reaction mixture to a suitable temperature ranging from about 25° C. to about 100° C.

4. The process according to claim 2, wherein the solvent is mixture of ethyl acetate and n-heptane.

5. The process according to claim 2, wherein the solvent is mixture of n-heptane and methyl tertiary butyl ether (MTBE).

6. A process for preparation of crystalline form-M5 according to claim 1, comprising:
   a) dissolving compound of formula-1 and methyl paraben in a solvent,
   b) optionally filtering the obtained solution, and
   c) isolating crystalline form-M5 of compound of formula-1.

7. The process according to claim 6, wherein the solvent is selected from alcohol solvents, ester solvents, nitrile solvents, ketone solvents, polar solvents, polar aprotic solvents, hydrocarbon solvents, ether solvents or mixture thereof; and optionally heating the reaction mixture to a suitable temperature ranging from about 25° C. to about 100° C.

8. The process according to claim 6, wherein the solvent is ethyl acetate.

9. The process according to claim 6, wherein the solvent is acetonitrile.

10. A pharmaceutical composition comprising crystalline form-M5 of compound of formula-1 of claim 1 and at least one pharmaceutically acceptable excipient.

11. A method of treating a patient comprising administering to the said patient a therapeutically effective amount of crystalline form-M5 of compound of formula-1 of claim 1.

12. The crystalline form-M5 of compound of formula-1 of claim 1 is further characterized by its PXRD pattern in accordance with FIG. 7.

\* \* \* \* \*